United States Patent [19]

Glater et al.

[11] Patent Number: 5,334,130
[45] Date of Patent: Aug. 2, 1994

[54] CENTRIFUGAL VACUUM CONCENTRATION WITH HOLDER ASSEMBLY

[75] Inventors: Michael Glater, Brooklyn; Carlos Barreda; Yury Zlobinsky, both of Massapequa, all of N.Y.

[73] Assignee: Savant Instruments, Inc., Farmingdale, N.Y.

[21] Appl. No.: 882,596

[22] Filed: May 13, 1992

[51] Int. Cl.⁵ .................... B04B 1/18; B01D 1/00
[52] U.S. Cl. .......................... 494/4; 159/6.1; 159/DIG. 16; 202/205; 494/16; 494/61
[58] Field of Search ............. 159/6.1, DIG. 16; 202/205; 494/16, 61, 4; 422/72; 436/177; 269/21

[56] References Cited

U.S. PATENT DOCUMENTS

| | | | |
|---|---|---|---|
| 879,255 | 2/1908 | Goodman | 494/4 |
| 2,507,309 | 5/1950 | Larsson | 494/16 |
| 2,635,617 | 4/1953 | Condell | 494/4 |
| 2,664,905 | 1/1954 | Harstick | 494/4 |
| 3,720,502 | 3/1973 | Gropper et al. | 494/16 |
| 3,849,072 | 11/1974 | Ayres | 494/16 |
| 3,901,434 | 8/1975 | Wright | 494/16 |
| 4,193,538 | 3/1980 | Schwarz | 494/16 |
| 4,226,669 | 10/1980 | Vilardi | 159/44 |
| 4,327,661 | 5/1982 | Boeckel | 494/16 |
| 4,690,670 | 9/1987 | Nielsen | 494/16 |
| 4,724,048 | 2/1988 | Helmich | 202/176 |
| 4,927,406 | 5/1990 | Glen et al. | 494/16 |
| 4,990,132 | 2/1991 | Unger et al. | 494/17 |
| 5,017,198 | 5/1991 | Schieg et al. | 55/21 |
| 5,048,804 | 9/1991 | Ito | 269/21 |
| 5,084,133 | 1/1992 | Guy et al. | 202/234 |
| 5,137,604 | 8/1992 | Meeks et al. | 159/6.1 |
| 5,211,808 | 5/1993 | Vilardi et al. | 494/61 |

Primary Examiner—Virginia Manoharan
Attorney, Agent, or Firm—George J. Brandt, Jr.; Thomas R. Morrison

[57] ABSTRACT

A vial holding a material such as an organic liquid-containing biological specimen is received in the receptor of a holder assembly, the assembly further including a centrifugal valve. The holder is mounted on a rotor in a centrifugal vacuum concentrator and the specimen is then subjected to a treatment such as drying in the vacuum chamber. Vapor from the drying vents into the concentrator vacuum chamber, the centrifugal valve which is a normally closed component opens due to imposition thereon of centrifugal force created during and attending rotor speed above a certain RPM. At completion of the treatment and before the rotor falls from its certain RPM, a dried material protective gas blanket can be flowed into the vial, the valve closing to seal the vial and protected contents when RPM of the rotor falls below the certain RPM. The valve also is a pressure relief valve that functions when the rotor is at rest to open when a pressure is present in the vial at or above a predetermined value to relieve the pressure and thereby protect the vial and its contents. The holder assembly can serve as a sealed, protected specimen package facilitating handling and storage of the specimen.

11 Claims, 5 Drawing Sheets

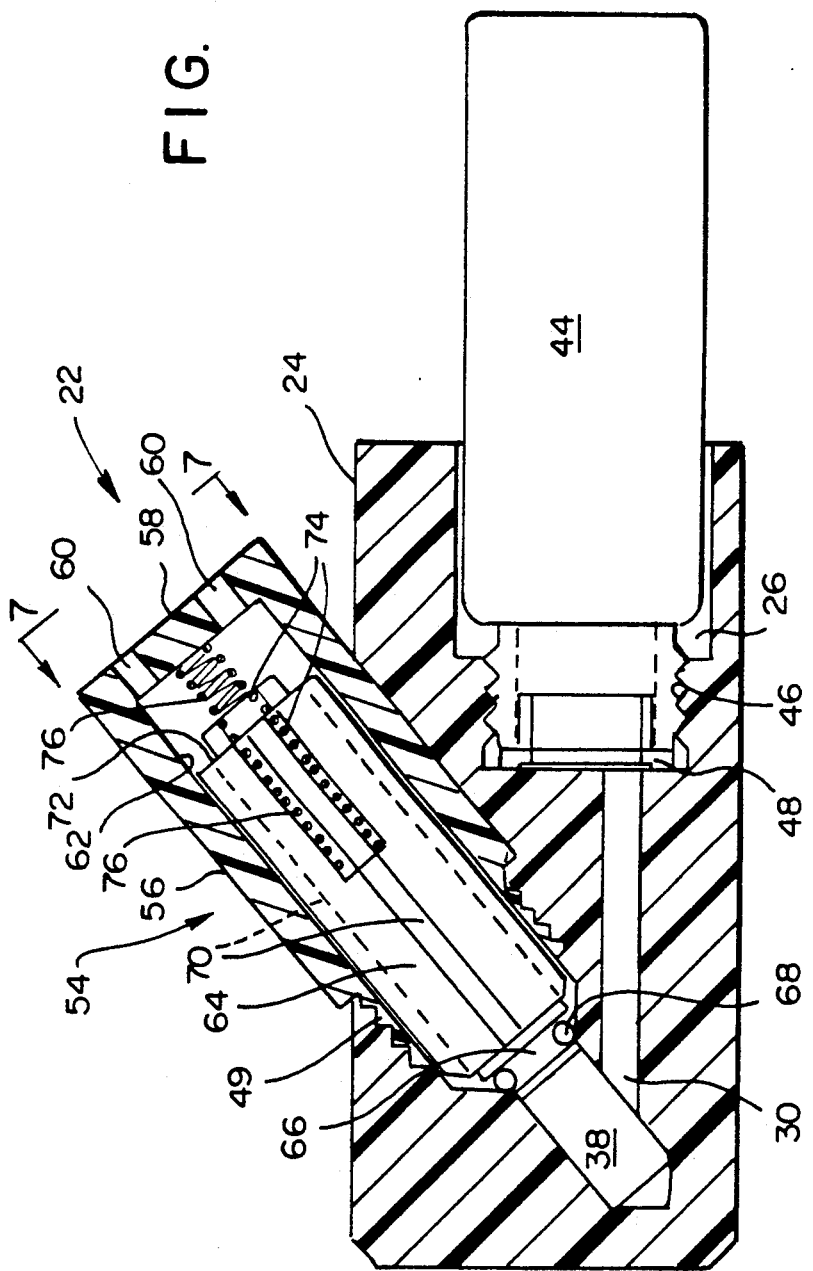

CENTRIFUGAL VACUUM CONCENTRATION WITH HOLDER ASSEMBLY

BACKGROUND OF THE INVENTION

The present invention relates to utilization of a centrifugal valve in conjunction with processing liquids-containing materials such as concentrating same in a vacuum chamber, as well as in other procedures wherein control of flow inlet to/outlet from a container such as a vial holding the materials is required or desired. Representative of such is deprotection of a synthetic oligonucleotide.

There are different procedures to which materials such as biological specimens can be subjected. For example, a biological material or specimen may be contained in an organic liquid. To recover the specimen, it and the liquid containing same already present in a container such as a vial can be subjected to a centrifugal vacuum concentration in a vacuum chamber, the vial being held on a rotor which is rotated during the concentration. When concentration is completed, rotation is stopped and the vacuum chamber vented. In some instances, an inert gas can be admitted to the chamber prior to venting to provide a protective blanket of, e.g., nitrogen over the dried specimen. The vial then can be capped to protect the vial contents until further specimen use time. The handling of the vial for capping allows possibility that contamination of the contents can take place.

Another handling of a specimen can be a hydrolysis operation. As a preliminary to heating the specimen in a sealed container, it is required that any air environment in the container be withdrawn and replaced with an inert gas blanket. To do this can involve using special equipment for evacuating the container.

Other protocols relating to biological material and the handling of same can present possibility of contamination or specimen material loss through spillage or other human error.

It is desirable then that means and method be provided to allow packaging or containment of materials in containers which permit many commonly used procedures be practiced, such as centrifugal vacuum concentration, during which flow access to and from the container is possible to introduce or remove particular gas/vapor media and at the end of the procedure the container be gas-tight sealed and thereafter handled in ordinary manner without hazard of contaminating or losing the contents.

OBJECTS AND SUMMARY OF THE INVENTION

Accordingly, it is an object of the invention to provide method and means by which outflow and inflow to containers wherein materials being subjected to procedures such as drying in a centrifugal vacuum concentrator can be controlled during such procedures, with the container being sealed at the termination of the procedure.

It is a further object of the invention to provide a method and means with which materials being, e.g., dried in a centrifugal vacuum concentrator conveniently can be handled during and after such and which effectively eliminates possibility of contaminating the so treated materials.

It is a still further object of the invention to provide a holder assembly which receives both a material container and a centrifugal valve and is mountable on a periphery part of a rotor of a centrifugal vacuum concentrator, the centrifugal valve opening during rotor revolution due to an imposed centrifugal force acting on the valve thereby to allow vapor outflow from the container during drying and also inletting of a protective gas under pressure to the container if necessary, the valve also opening if the rotor is at rest responsive to a pressure presence above a predetermined value in the container, as one caused by a reaction occurring in he container so that the pressure is relieved.

Briefly stated, there is provided that a vial holding a material such as an organic liquid-containing biological specimen is received in the receptor of a holder assembly. This holder assembly also carries a centrifugal valve. The holder is mounted on a rotor in a centrifugal vacuum concentrator and the specimen is subjected to a treatment in the vaccum chamber, such being, for example the concentration of drying of the specimen. Vapor from the drying vents into the vacuum chamber. The centrifugal valve which is normally closed opens due to imposition thereon of centrifugal force created during rotation of the rotor above a certain RPM. At completion of the treatment and before rotor speed falls below the certain RPM, a dried material protective gas blanket can be flowed into the vial via the open valve with the valve closing to seal the vial and contents when the RPM falls below the certain value. the valve also functions as a pressure relief valve when the rotor is at rest opening when a pressure is present in the vial at or above a predetermined pressure value to relieve the pressure and thereby protect the vial and its contents. The holder assembly can serve as a sealed, protected specimen package facilitating handling and storage of the specimen.

In accordance with these and other objects of the invention, there is provided a holder assembly for use in a centrifugal vacuum concentrator. The concentrator includes a sealable vacuum chamber and a rotor in the chamber on which a liquid-containing material is supported to concentrate same when the rotor is rotated and a condition of vacuum imposed on the chamber by connecting it with a vacuum pump. The holder assembly is mountable on the rotor and it has a receptor housing, the receptor housing having a passage therein. A vial holds the liquid-containing material and the vial has an opening therein. Means are provided for removably securing the vial to the receptor housing with the vial opening in communication with the receptor housing passage. A centrifugal valve is carried by the receptor housing and it includes a movable valve element. Bias means normally urge the valve element to a port blocking position of a port communicating the receptor passage with an outlet therefrom to the vacuum chamber. The bias means maintains the valve element in port blocking position in opposition to a counter bias effect of one of a pressure presence in the receptor housing passage which is any pressure in a range of pressures below a predetermined pressure value and a centrifugal force which is any force in a range of centrifugal forces below a certain magnitude acting on the valve element during rotor rotation and tending to urge it counter to the urging of the bias means. The bias means also maintains the valve element in port blocking position in opposition to combinations of a particular range pressure presence and a particular range centrifugal force.

According to a feature of the invention, there is further provided in a method for concentrating a liquid-containing material in which the material is supported on a rotor in the vacuum chamber of a centrifugal vacuum concentrator and the rotor rotated while a condition of vacuum is imposed on the chamber by connecting it to a vacuum pump, the securing of a vial containing the material and having an opening therein, to a receptor of a rotor mountable holder assembly, this with the vial opening in communication with a passage in the receptor. The holder assembly includes a centrifugal valve carried by the receptor and the centrifugal valve includes a valve element. This valve element is normally biased to a position blocking a receptor port communicating the receptor passage with an outlet therefrom to the vacuum chamber. The valve element blocking position is maintained in opposition to a counter bias effect of one of a pressure presence in the receptor passage which is any pressure in a range of pressure below a predetermined pressure value and a centrifugal force which is any force in a range of centrifugal forces below a certain magnitude acting on the valve element during a rotation of the rotor, the valve element also being maintained in blocking position in opposition to combinations of a particular range pressure and a particular range centrifugal force. A condition of vacuum is imposed on the vacuum chamber and the rotor is rotated up to at least a speed thereof which produces centrifugal force acting on the valve element in excess of the said certain magnitude and in correspondence to that, the receptor port is unblocked. With that unblocking, vapor form of liquid can be drawn from the vial through the receptor passage and outwardly into the vacuum chamber. This rotor speed is maintained at least until the material is dried.

Upon completion of drying but before reduction of rotor speed, and while vacuum condition is maintained in the vacuum chamber, a positive pressure flow of an inert gas can be admitted to the vacuum chamber so this gas can access the vial through the unblocked receptor port and receptor passage and establish a protective blanketing of the dried material.

Also, upon completion of drying vacuum condition can be maintained in the chamber and rotor speed reduced so that a vacuum condition remains in the vial when the valve blocks the port on rotor slow down.

A further feature of the invention provides that in a method for treating a biological specimen in a closed container which includes a treatment procedure requirement for a particular gas environment presence or absence of an environment presence in the container that the container with biological specimen therein be secured to a receptor of a holder assembly with an opening in the container communicating with a passage in the receptor. The receptor carries a centrifugal valve including a valve element bias blocking an outlet port of the passage. The holder assembly is disposed on a rotor in a vacuum chamber and a condition of vacuum imposed on the chamber. The rotor is rotated at a speed in excess of a predetermined RPM so a centrifugal force imposed on the centrifugal valve element at said excess speed overcomes the valve bias whereby the outlet passage outlet port becomes unblocked and the chamber vacuum condition effects evacuation of environment presence in the container. Optionally then a pressure flow of a particular gas is introduced into the vacuum chamber while the rotor speed is in excess of the predetermined RPM from whence it can access the container through the unblocked port before the port becomes blocked on reduction of rotor speed below said predetermined RPM.

The gas admitted to the container can be an inert gas such as nitrogen.

The centrifugal valve is also operable in absence of centrifugal force thereon to maintain bias blocking of the outlet passage port in the presence of a positive pressure in the container up to a predetermined pressure value so that if that pressure value be exceeded, the bias will be overcome, the port unblocked and the pressure thereby relieved in the container.

An additional feature of the invention provides a containment package for holding material normally isolated from extra package environment but embodied with allowance for selectively accessing an internal material containment space thereof with the extra package environment responsive to necessity for admission of gas to the containment space or expulsion of gas therefrom. The containment package is comprised as a holder assembly which includes a receptor body having a socket therein in which a first end part of a container for holding the material and defining the containment space is received in a gas tight fit of the container with the socket. An opening in the container communicates with an internal passage in the receptor body. The receptor body has a second socket which includes an interior seat surface and the seat surface has a port communicating the second socket with the receptor body internal passage. A centrifugal valve is received in gas tight fit of a valve housing with the second socket and the valve includes a valve element movable in the housing. Bias means normally urge the valve element to a position blocking the seat surface port with the bias means being operable to maintain the valve element in port blocking position in presence of a gas pressure in the containment space up to a predetermined gas pressure value. The valve element is moved to a port unblocking position by containment space gas pressure at or in excess of said predetermined value whereby gas can outflow the containment space in a flow transit by way of the receptor body internal passage through the seat surface port for entry into the valve housing and then into the extra package environment by passage through a ported opening in the valve housing remote from the seat surface port. The bias means is insufficient to maintain the valve element in port blocking position if the valve element is subjected to centrifugal force imposed thereon in excess of a predetermined magnitude when the holder assembly is rotated about a fixed axis above a certain RPM so that a gas presence in the containment space can be drawn therefrom in the said flow transit to a vacuum extra package environment or a gas which is protective of the material in the containment can be inflowed thereto in a reverse transit flow from an extra package environment which is an environment of such gas at a pressure above any in the containment space.

The above, and other objects, features and advantages of the present invention will become apparent from the following description read in conjunction with the accompanying drawings, in which like reference numerals designate the same elements.

BRIEF DESCRIPTION OF THE DRAWINGS

FIG. 6 is a vertical longitudinal sectional view of the holder assembly with a sample vial and centrifugal valve secured thereto; and FIG. 7 is an end view of the centrifugal valve carrier as viewed in the direction of line VII—VII in FIG. 6.

DETAILED DESCRIPTION OF THE PREFERRED EMBODIMENTS

The present invention is used in conjunction with handling, processing and packaging of numbers of types of materials. It can be employed with centrifugal vacuum concentration of organic liquid-containing biological specimens, with a simple vacuum drying of a material but with a drying termination wherein the dried material is in that state packaged in a gas tight contained condition and thus, preserved from normal environmental agents that can cause contamination, or it can be employed to introduce a required environment such as an inert gas into a biological-containing specimen which is to be subjected to a hydrolysis procedure or reaction where presence of air in the reaction container cannot be tolerated. It can be used where oligonucleotides are deprotected, such involving reacting the protected oligonucleotide with ammonium hydroxide to cleave the protecting groups therefrom followed by vacuum concentration, these procedures being practiced with the reaction and concentration materials disposed in normal environment excluded surroundings, the resultant deprotected oligonucleotide being packed in a gas tight container without need for any handling by laboratory personnel from outset of reaction until the deprotected oligonucleotide is protectively sealed in the container.

The holder assembly and procedure utilizations disclosed herein also can be used for processing synthetic proteins.

The flexibility of procedure possibility and protected packaging of materials referred to above is achieved with use of a special holder assembly in which the material container is received and held during processing, this holder assembly also carrying a centrifugal valve that bars unwanted extra processing and handling environment agents from investing the container. The centrifugal valve functions to admit desired gas inflow to the container or withdrawal of an unwanted environment from the container as an adjunct of processing. The valve also can function to relieve an excess pressure build up in a sealed container where an intended reaction is being carried out in the container.

The active processing commonly, but not exclusively, will be done in the vacuum chamber of a centrifugal vacuum concentrator.

Figure 1:
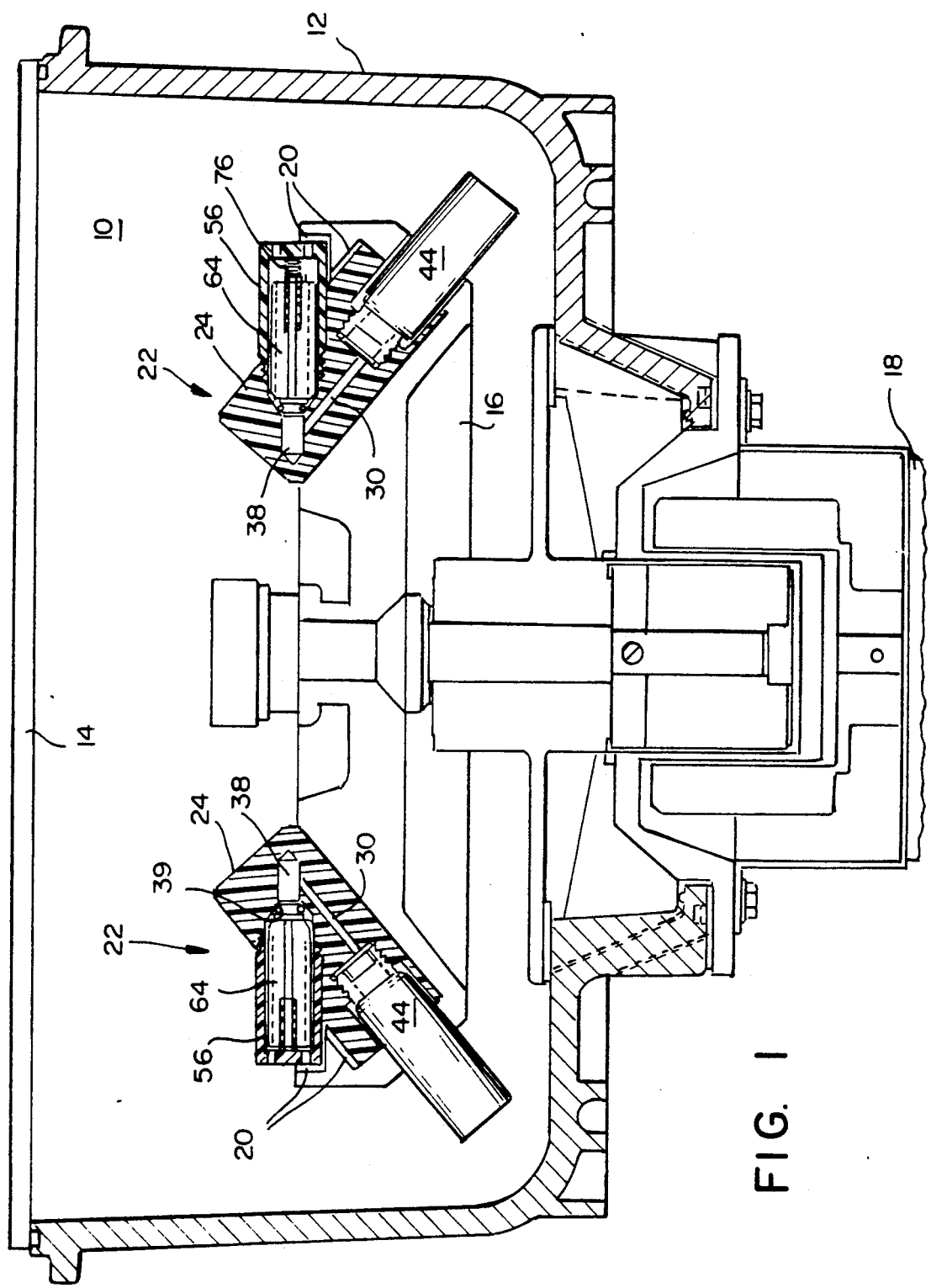
FIG. 1 is a vertical central sectional view of a vacuum chamber in which concentration of, e.g., volatile liquid containing materials can be carried out, with holder assemblies in which the materials are held during concentration being depicted received at opposite diametrical locations on a chamber rotor, the respective centrifugal valves depicted at the left and right opposite locations being, respectively, in valve open and valve closed positions.
Figure 2:
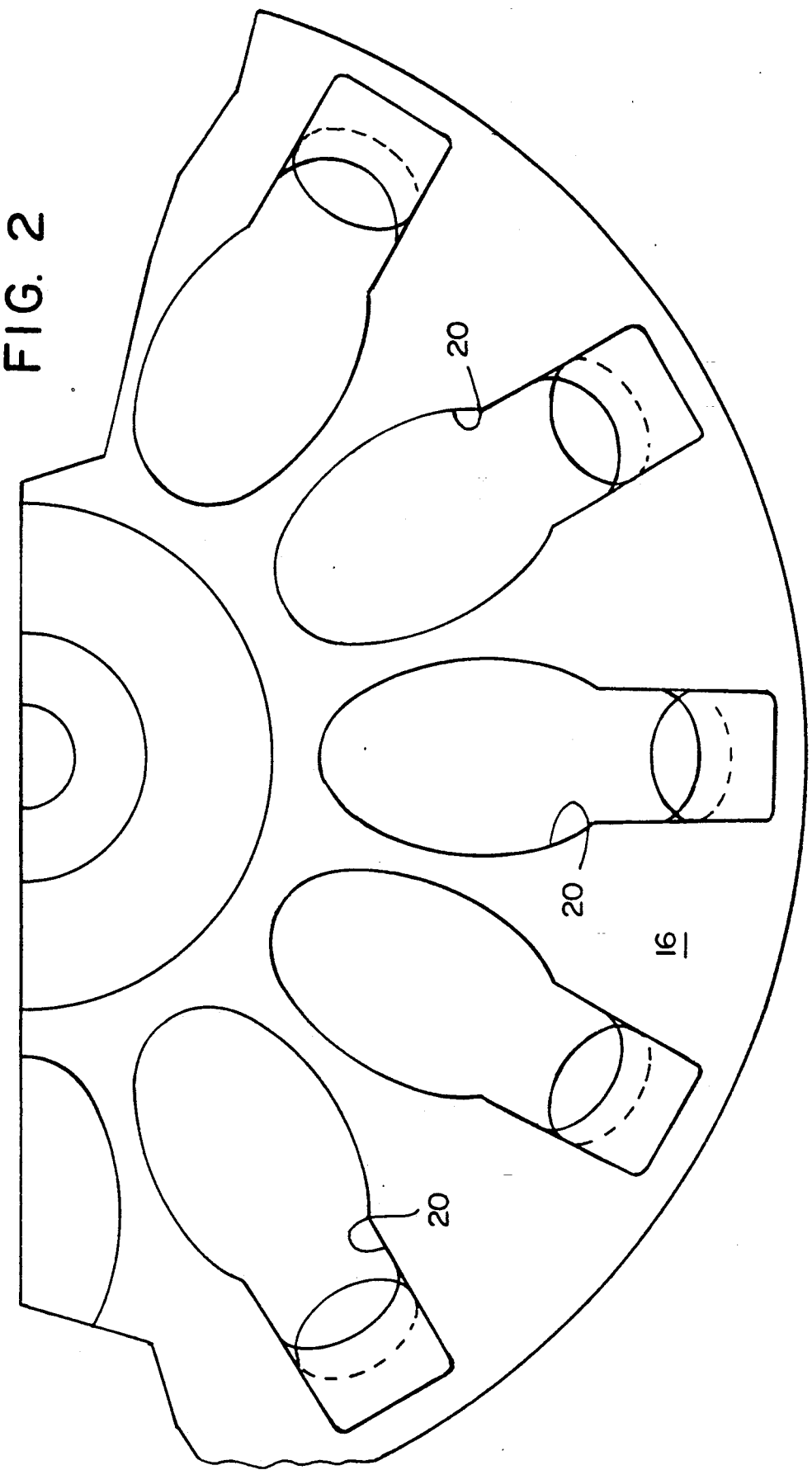
FIG. 2 is a fragmentary top plan view of the chamber rotor shown in FIG. 1 illustrating the individual slots provided therein for receiving holder assemblies.
Figure 3:
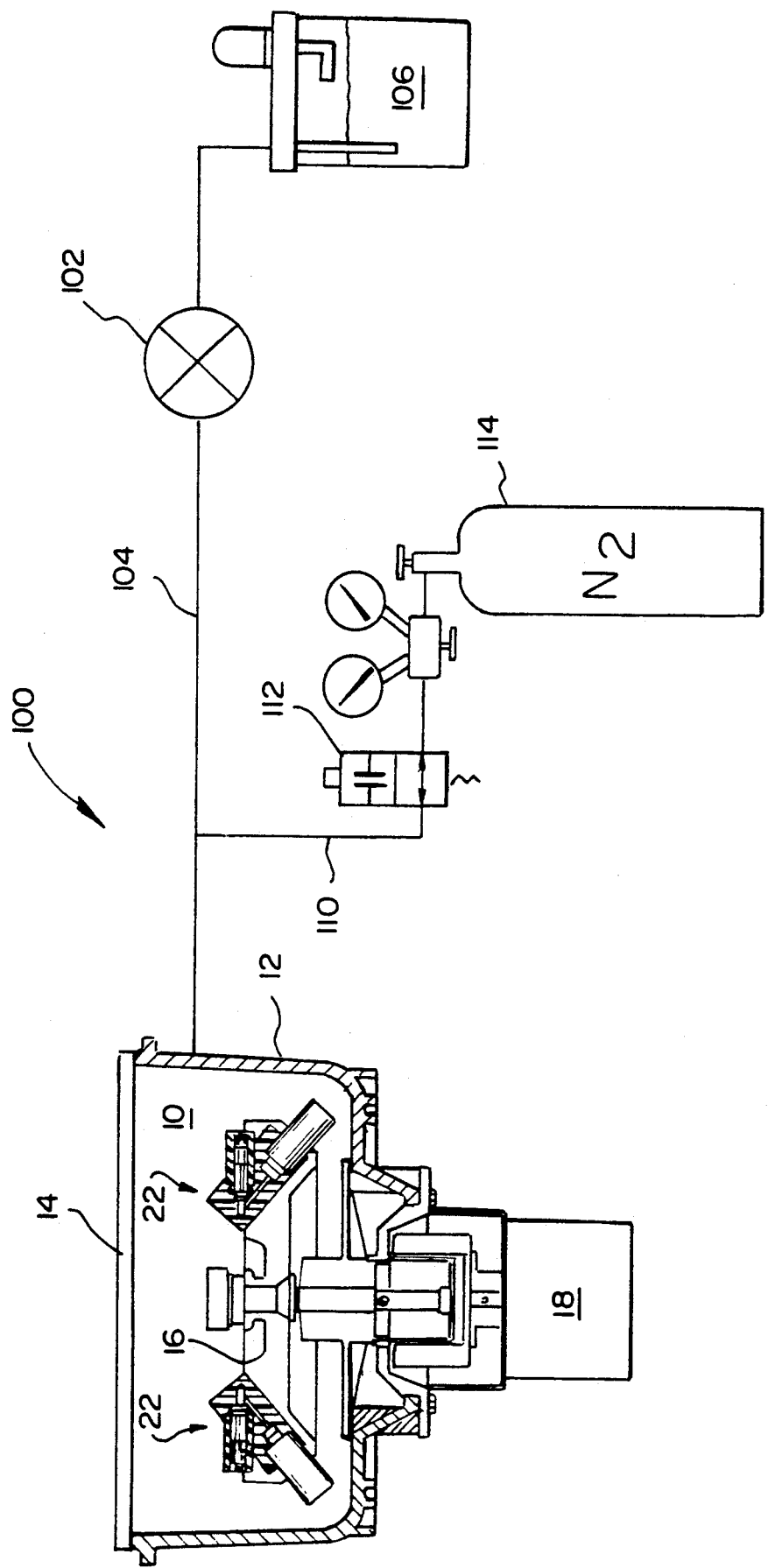
FIG. 3 is a diagrammatic, partly vertical sectional depiction of centrifugal vacuum concentrator apparatus in which volatile liquid-containing materials concentration can be carried out.

Referring now to FIG. 1, there is shown a vacuum chamber 10 defined by vessel 12 and including a cover 14, the chamber being a component in the centrifugal vacuum concentrator system depicted in FIG. 3. A rotor 16 in the chamber is driven by a motor 18, e.g., by a magnetic coupling drive so that the vessel is unpierced at the bottom insuring attainment and maintenance of high vacuum condition in the chamber.

Rotor 16 includes a circular array of slotted openings 20 which serve to receive and support the after described holder assembly 22 shown in detail in FIG. 6. The slotted openings 20 are inclined to the horizontal to a certain degree and cooperate with the holder assembly to provide that a centrifugal valve carried by each holder assembly disposes horizontally and radially on the rotor. Description of the holder assembly 22 will be given next.

Figure 4:
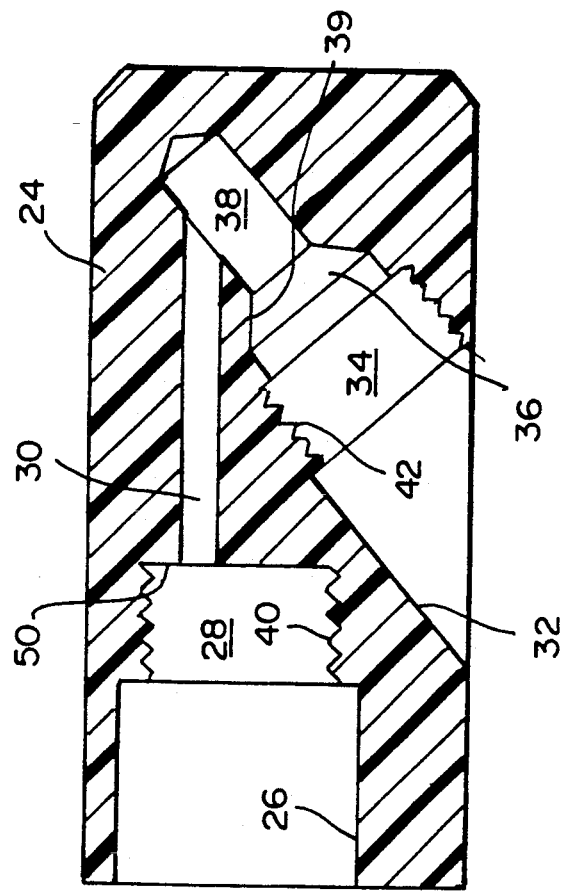
FIG. 4 is a vertical central sectional view of the holder assembly receptor or cap part to which both the sample vial and the centrifugal valve are threadedly secured.
Figure 5:
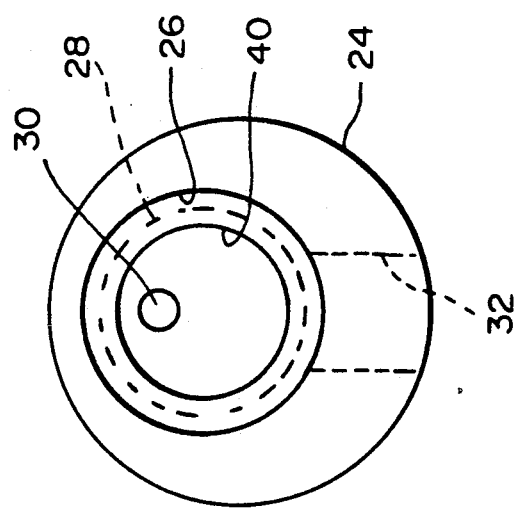
FIG. 5 is an end view of the receptor part looking from the left in FIG. 4.

The holder assembly includes a receptor or cap member 24 (detailed in FIGS. 4 and 5) which receptor is an elongated member, e.g., being of cylindrical profile. Receptor 24 can be made of a moldable plastic material such as polyphenol sulphide, polypropylene, polytetrafluoroethylene and the like. The receptor could also be machined from stainless steel.

The receptor body has a lengthwise directed bore or socket inclusive of stepped bore segments 26, 28 and 30, the last-mentioned being of much reduced diameter compared to segments 26, 28 and being eccentrically located in the receptor. The receptor body also includes a second, lateral bore or socket comprised of bore segments 32, 34, 36, and 38. The bore segment 36 includes a seat surface 39 for purpose to be given below, and the bore segments 30, 38 constitute a receptor interior passage. Where bore segment 38 merges with bore segment 36 adjacent seat surface 39 such constitutes a receptor port. Bore segments 28 and 24 are female threaded as at 40, 42 which structure is part of securement means by which a vial and a centrifugal valve are secured to the receptor.

With reference to FIG. 6, the holder assembly 22 receives a container or vial 44 that can contain a biological specimen, a material to be dried or like. The vial 44 which commonly will be a glass member, has a neck portion terminating in a vial opening, the neck portion being male threaded as at 46 so that the vial can be secured to receptor 24 in gas tight fit therewith. To enhance the gas tight securement, a seal member such as a gasket piece 48 interposes the neck portion and blind face part 50 of bore segment 28.

The holder assembly also receives secured thereto, a centrifugal valve member shown generally at 54 and which comprises a carrier or sleeve 56 having threads 49 at an end engageable with the receptor threads 42 for securing the sleeve to the receptor, this too being a gas tight fit. Sleeve 56 conveniently is made of the same material as the receptor.

Sleeve 56 is provided at its end opposite the threaded end with a transverse end wall 58 which end wall includes a circle of ported openings 60. Within bore 62 of the sleeve is slidably movably carried elongated valve element 64, the valve element being closely fitted to the bore surface. Valve element 64 is provided at one end with a reduced diameter annular part 66 which is encircled by a seat structure engageable O-ring 68. A number of longitudinal slots 70 extend longitudinally of the valve element at its outer surface, these slots, e.g., four in number, are spaced around the valve element body and they serve as flow courses for gas flow out of or into the vial 44 all as will be detailed at length later.

At an opposite end of the valve element 64, it has a reduced diameter tip as at 72, this tip and a length of the valve element body extending therefrom being centrally, longitudinally blind bored as at 74 so that bore is receptive of a bias unit compression spring 76 which in addition to filling the blind bore 74 extends beyond the valve element opposite end into engagement with an inner face of end wall 58. Spring 76 exerts bias on the valve element to normally move it into and maintain port blocking position in which the O-ring 68 is seated on seated structure 39. Thus flow communication of the receptor interior passage with environment exterior of the holder assembly is blocked.

In FIG. 6 the centrifugal valve is in closed or port blocking condition as is the valve at the right side of the rotor in FIG. 1. In FIG. 1, the centrifugal valve at the left side of the rotor is for illustrative purpose shown in its open position wherein it is seen the valve element tip 72 is abutted against the inner face of sleeve end wall 58.

Referring now to FIG. 3 there is shown a system 100 in which the various treatments of materials can be practiced. This centrifugal vacuum concentrator system includes the vessel 18 fitted with the components above described with reference to FIG. 1 and a vacuum pump 102, e.g., three stage diaphragm pump connected as by line 104 to the interior of vacuum chamber 10. The discharge of pump 102 in this particular system arrangement is to a bubble trap unit 106 which vents to normal atmosphere. Other end locations for pump discharge can be used as well. A branch line 110 off the main line 104 is connected to a two position slide valve 112. Valve 110 in one position vents line 104 and hence, chamber 10 to atmospheric air. In the other position, it connects the chamber to a pressurized source of an inert gas such as nitrogen in a tank 114. System 100 can be used in a drying or concentration operation. It can be used in other ways as will be discussed below.

Before providing description on the various ways and manner of using the system and holder assembly to useful purpose, some detailing of the function of the centrifugal valve first will be given.

With continuing reference being had to FIGS. 1 and 6, the centrifugal valve serves to block or unblock the port by which flow communication can be had between the receptor interior passage 30, 38 and a space outside the receptor, such space usually being vacuum chamber 10. With the port unblocked, a gas or solvent vapor etc can flow from the vial through interior passage 30, 38, through the port along the valve element slots 70 and through sleeve end wall ports 60 into the vacuum chamber. Where a requirement is for flowing gas into the vial, the flow course is reversed.

As indicated above the centrifugal valve normally will be closed, that is, the bias unit of spring 76 will urge the valve element to port blocking position. This blocking will be maintained against two forces that would tend to urge the valve element counter to the urging of the bias of spring 78 so as to unblock the port. The first such force is a pressure presence in the vial, a condition, e.g., attending a reaction procedure taking place in the vial. Illustrative of such is a hydrolysis procedure or the reaction that accompanies oligonucleotide deprotection.

It is not intended that in such procedures the valve open since there is usually no purpose to deliberately vent reaction materials from the vial. Rather, the centrifugal valve functions as a pressure relief valve. There is an expected range of pressures that can be expected to exist in the vial during a given procedure. As long as these are all that exist, the valve should remain closed. On the other hand, a pressure build up within the vial to a predetermined pressure value represents a pressure such as can lead to destruction of the vial with consequent loss or contamination of material being reacted and in the case of biological materials something to be avoided.

With that in mind the spring 76 is selected to bias valve element to blocking position whenever the pressure presence is below the predetermined value. Generally, the predetermined pressure value will be one some fair measure above the expected pressures produced during reaction. For example, where expected pressures are 25–35 psig, the valve will be designed to remain closed until pressure reaches about 45 psig at which point it will open to relieve the pressure, with relief outflow passing into the chamber 10. The foregoing valve functioning will be that when the rotor 16 is at rest. During rotor rotation a condition attending a drying operation, the rotor will be rotated. Valve opening there is produced by a second force acting to counter the effect of the spring bias.

During rotor rotation, centrifugal force acts on the valve element. When that centrifugal force is one below a predetermined magnitude, its imposition on the valve element is not enough to overcome the bias effect of the spring. This is something that holds for rotor RPM speeds below a certain RPM such as a rotor speed during build up to an operating speed. Once the rotor speed reaches the certain RPM, the valve will be opened because the centrifugal force imposition overcomes the spring effect which is insufficient to prevent valve element unblocking movement. During a drying operation, the valve must be open so that vapor form solvent can be drawn from the vial by the effect of vacuum in chamber 10.

The foregoing is further understood by assuming that a drying rotor speed is 1650 RPM, and that the certain speed at which centrifugal force imposition on the valve element is of certain magnitude, is 1100 RPM. This means that during rotor speed build up, the valve stays closed in initial speed up. Once the rotor reaches a speed of 1100 RPM, the valve becomes completely opened. Partial opening in the assumed situation may begin at a lower speed of around 900 RPM.

The particular speed at which it is desired the valve open can be varied depending on particular procedure requirements and, on the weight of the valve element. Regarding valve element weight, the faster the rotor is rotated, the lighter the valve element can be made since for a given or desired valve opening magnitude of centrifugal force, increase in speed produces the such force with less weight of valve element.

The centrifugal valve also will open to unblock the receptor port when a combination of the force of a pressure presence in the receptor passage and centrifugal force acting on the valve element are present. These forces will be for the one a pressure presence in a range of such, which is below the predetermined pressure, and for the other a centrifugal force which is in a range of such below the certain magnitude. For example, the centrifugal valve may be designed to open with static pressure presence of 45 psig. Such a pressure presence in the receptor passage may only be 38 psig. Further rotor start up may be in progress but rotor speed for centrifugal force opening of the valve be still some hundreds of RPM away. Neither of these force parameters by itself is sufficient to overcome the spring bias. But together they produce opening. The 38 psig effect on the spring plus the centrifugal force effect are enough to crack the valve, i.e., move the valve element away from the seat. With that happening, the 38 psig is relieved to a degree of say falling to 35 psig. But with the valve opening, more area of the valve element tip end is exposed and the force effect of the 35 psig acts on this greater area and produces greater urging of the valve element counter to the spring bias, and hence, fuller opening of the valve. It is understood that once rotor RPM reaches a speed associated with the certain magnitude of centrifugal force, the valve opens fully without regard to any pressure in the receptor passage.

The use of the centrifugal valve and the holder assembly 22 allow a number of options of use in materials handling, processing and packaging. Illustrative are:

1. Centrifugal vacuum concentration of an organic liquid solvent-containing biological material is carried out in the usual way to dry the biological material. During concentration the centrifugal valve is open to allow solvent vapor form to pass from the vial to the vacuum chamber. Before shutting down the concentrator, nitrogen from pressurized source 114 can be admitted to the vacuum chamber 10 and fills the environment of vial 44 to protectively blanket the dried material. With rotor slowdown incident system shutdown, the centrifugal valve closes and the vial thus becomes sealed. The dried biological material is now packaged in a sealed container and can be handled further or stored without resort to special handling need. The holder assembly itself is the package.

2. A specimen to be hydrolyzed or otherwise reacted is placed in the vacuum chamber 10. The rotor 16 is started and connection made to the vacuum pump. The vial environment is evacuated and replaced with inert gas. The system is shutdown with attendant valve closure. Reaction heat can be applied to the specimen to carry out the reaction. If a pressure builds up in the specimen container beyond a predetermined value, it will be relieved. On completion of the reaction, the specimen is already safely packaged until a next use is to be fulfilled.

3. A specimen reacted as described in 2 could if such is the protocol, be concentrated in the chamber without need of disturbing the holder assembly. A combined 2 and 3 procedure can be deprotection of an oligonucleotide, an example of which will be described shortly.

4. A specimen or material which simply needs be stored under vacuum is placed in a holder assembly on the rotor and the system is started. The container or vial holding the material is evacuated. With system shutdown, the container becomes sealed with vacuum condition therein.

An example of how the invention is useful for synthetic oligonucleotide deprotection is discussed now.

In oligonucleotide synthesis, biologically active oligonucleotide must be cleaved or removed from a support, and this commonly is effected by reaction of the product with concentrated ammonium hydroxide at room temperature for about an hour. Complete deprotection of the synthetic oligonucleotide requires that thereafter the protecting benzoyl and isobutryl base groups be cleaved from the oligonucleotide. The last-mentioned cleavage is carried out by reacting the oligonucleotide with concentrated (e.g., 27%) ammonium hydroxide in a capped vial that is heated for a period of time.

The ammonium hydroxide is added to a vial containing the oligonucleotide that has been cleaved from its support. The vial is secured to a holder 22 and the holder mounted on rotor 16 of system 100. With the system shut down but chamber 10 covered, heat is applied to the contained oligonucleotide with heating means in the chamber to cause reaction of the ammonium hydroxide with the protecting groups. It is here noted that the vial 44 is mounted in receptor 24 in such manner that an appreciable portion of the vial external surface is exposed, and this is done to promote good heat transfer into the vial. The heating can be effected at temperatures in a range of about 40–100 degrees C. The time of heating will vary according to the protocol involved. For example, heating at about 55 degrees C. may take anywhere from 5 to 12 hours to produce the cleavage. At higher temperature say about 85–100 degrees C., cleavage will be achieved in shorter time possibly as low as in 45 minutes.

During heating, the pressure in the vial will rise in correspondence to the temperature, this pressure being about 30 psig where temperature is 55 degrees C., and it can be 68–70 psig where temperature is 85 degrees C. In any event, the centrifugal valve will be designed not to open unless pressure in the vial is at some value higher than what is expected to exist in the vial. Thus, and in the case where 55 degrees C. heating is used and expected pressure in the vial is 30 psig, the valve would be designed to relieve static pressure at or above 45 psig. The valve is a safety device in this respect provided to protect the vial and its contents. It is not desired that any venting of the vial occur in normal reaction procedure.

At the end of the cleavage heating, the oligonucleotide will be concentrated. In that processing, the system will be started up by rotating the rotor and connecting the chamber to the vacuum pump. At the certain RPM of the rotor, the valve will open completely and vapor form solvents can be drawn from the vial. The high rotor speed serves during the concentration to prevent "bumping" or pull out of solid or liquid form material from the vial due to the vacuum in the chamber, the centrifugal force imposed on this material keeping it from "bumping". Vapor of course is drawn out. Concentration can take some period of up to 2 or 3 hours. When the oligonucleotide is dried in which form it will be present as a discrete form solid intermingled with discrete solid form protection groups material, and before the system is shut down, nitrogen flow under pressure will enter the vacuum chamber and pass through the receptor structure into the vial to protectively cover the dried material. At shutdown the rotor slows to speed at which the valve closes this being while the chamber is still under vacuum pump influence. The oligonucleotide is now packaged in a protected gas tight package unit.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A holder assembly for use in a centrifugal vacuum concentrator, said centrifugal vacuum concentrator including a sealable vacuum chamber, and a rotor in the chamber on which a liquid-containing material can be supported to concentrate same when the rotor is rotated and a condition of vacuum is imposed on the chamber by connecting a vacuum pump to the chamber, the holder assembly being mountable on the rotor, said holder assembly comprising a receptor housing, the receptor housing having a passage therein, a vial for holding the liquid-containing material, the vial having an opening therein, means for removably securing the vial to the receptor housing with the opening therein in communication with the receptor housing passage, and a centrifugal valve carried by the receptor housing and including a movable valve element, and bias means normally urging the valve element to a port blocking position of a port communicating the receptor housing passage with an outlet therefrom to the vacuum chamber, the bias means maintaining the valve element in port blocking position in opposition to a counter bias effect of one of or a combination of a pressure presence in the receptor housing passage which is a pressure in a range of pressures below a predetermined pressure value and a centrifugal force which is a force in a range of centrifugal forces below a predetermined magnitude acting on the valve element during rotor rotation and tending to urge it counter to the urging of the bias means, and the centrifugal valve being enclosed in a carrier secured to the receptor, an interior of the enclosure communicating with the receptor outlet, the enclosure having port means open to the vacuum chamber whereby an unblocked flow course exists between the vial opening and the port means whenever the valve element is out of port blocking position.

2. The holder assembly of claim 1 in which the means for removably securing the vial to the receptor housing includes companion securement structure on each.

3. The holder assembly of claim 2 in which the companion securement structure includes a male threaded part on one of said receptor housing and said vial, and a female threaded part on the other for receiving the male threaded part.

4. The holder assembly of 1 in which the receptor housing includes seat structure encircling the port communicating the housing passage with an outlet therefrom, the valve element having a seat engageable port blocking part.

5. The holder assembly of claim 4 in which the seat structure engageable part includes a deformable member which the bias means normally urges deformably against the seat structure to block the port.

6. The holder assembly of claim 5 in which the deformable member is an O-ring.

7. The holder assembly of claim 4 in which the valve element is an elongated component, the seat structure engageable part being defined by an end of said component, the bias means comprising a bias unit at an opposite end of the elongated component, one of the bias unit and elongated component being movable with respect to the other, the bias unit when in a held condition applying bias to the elongated component tending to move it to port blocking position.

8. The holder assembly of claim 7 in which the bias unit includes a spring loosely received in a bore at said opposite end of the component and engaged at an end with the component, an opposite end of the spring being engaged with a stop surface and normally urging the elongated component toward the seat structure.

9. The holder assembly of claim 1 in which the valve element and the carrier are elongated, the carrier being secured to the receptor at a first carrier end, the port means being located in an opposite second carrier end.

10. The holder assembly of claim 9 in which the carrier first end is secured to the receptor proximal the port in the receptor in a gas-tight relation between the two.

11. The holder assembly of claim 9 in which the receptor includes seat structure encircling the port, the valve element having a port blocking part at a first end thereof, there being a bias applying member engaged with the element at a location thereon remote from said port blocking part and with structure at the carrier second end whereby bias is applied to said valve element to urge its port blocking part into contact with the receptor seat structure.

* * * * *